United States Patent [19]

Tasto et al.

[11] 4,107,221

[45] Aug. 15, 1978

[54] REMOVAL OF OLEFIN OXIDE FROM CHLORINATED SOLVENTS

[75] Inventors: William D. Tasto; Thomas E. Morris, both of Lake Jackson, Tex.

[73] Assignee: The Dow Chemical Company, Midland, Mich.

[21] Appl. No.: 819,749

[22] Filed: Jul. 28, 1977

[51] Int. Cl.$^2$ ............................................. C07C 19/02
[52] U.S. Cl. ............................... 260/652 P; 568/867; 568/859
[58] Field of Search ............ 260/652 P, 635 R, 635 E

[56] References Cited

U.S. PATENT DOCUMENTS

| | | | |
|---|---|---|---|
| 2,909,572 | 10/1959 | Solomon | 260/652 P |
| 3,235,610 | 2/1966 | Wymore | 260/652 P |
| 3,851,043 | 11/1974 | Gunther | 260/635 E |
| 3,990,844 | 11/1976 | Cormany | 260/652 P |

*Primary Examiner*—C. Davis

[57] ABSTRACT

Minor amounts of olefin oxide such as butylene oxide are removed from a chlorinated solvent by contacting the solvent with the hydrogen form of a strong acid cation exchange resin in the presence of water.

6 Claims, No Drawings

REMOVAL OF OLEFIN OXIDE FROM CHLORINATED SOLVENTS

BACKGROUND OF THE INVENTION

This invention relates to a process for removing olefin oxide from a chlorinated solvent containing a minor amount of the same.

Chlorinated lower aliphatic hydrocarbon solvents such as perchloroethylene, trichloroethylene, 1,1,2-trichloroethane, and 1,1,1-trichloroethane are routinely inhibited against decomposition and reaction with metal containers by the incorporation of minor amounts, up to a few percent, of one or more stabilizers or inhibitors. These inhibiting additives are ordinarily compounds having a boiling point similar to that of the solvent and preferably not easily separable from the solvent by water extraction so that the inhibitor content remains relatively constant during the drycleaning, metal-degreasing, or other cleaning operations where such solvents are commonly used. These inhibiting additives include compounds such as nitromethane, dioxane, and alcohols, which chemically are relatively inert, and also more reactive compounds such as olefin oxides, for example, propylene oxide, butylene oxide, glycidol, and cyclohexene oxide which may serve in part at least as acid acceptors. These epoxides may be present in a stabilized solvent in concentrations up to about 5 percent by weight, but lower concentrations of about 0.01-0.5 percent are usually employed.

In some uses of such inhibited solvent compositions, for example, when the solvent is used in a chemical process either as a solvent or as a reactant, the presence of even a very small amount of a reactive impurity may be highly undesirable where it causes contamination of the product, inactivation of a catalyst, or similar harmful result. Vicinal epoxides such as those named above are examples of potentially disadvantageous reactive impurities. It is well known that olefin oxides react readily with water in the presence of a strong acid to form the corresponding diol, but the diol product and the acid catalyst may also be undesirable and not easily separable from the chlorinated solvent.

SUMMARY OF THE INVENTION

It has now been found that an olefin oxide is efficiently separated from a chlorinated lower aliphatic hydrocarbon containing a small amount of the same by contacting the chlorinated hydrocarbon with the hydrogen form of a strong acid cation exchange resin in the presence of water. The olefin oxide is thereby converted to the corresponding diol which is held by the resin so that the chlorinated hydrocarbon effluent from the resin bed is essentially free of both the oxide and the diol product.

DETAILED DESCRIPTION OF THE INVENTION

This invention provides a convenient means whereby a readily available conventional stabilized chlorinated solvent can be easily and efficiently purified to remove a deleterious impurity immediately before the chlorinated hydrocarbon enters a process reactor.

Any strong acid cation exchange resin in its hydrogen form is operable in the process. The term strong acid cation exchange resin is used in its usual sense; that is, meaning a resin capable of splitting salts. Commercially available examples of the class include DOWEX 50W, DOWEX MSC-1, DOWEX HGR, and DOWEX HCR resins produced by The Dow Chemical Company and similar resins made by other manufacturers.

The process is operable within a wide range of temperature between ambient temperature and a temperature as high as 165° C. Normally, it is carried out at or slightly above ambient temperature. Pressure is not a critical factor in the process and atmospheric or superatmospheric pressure may be employed.

The quantity of water present need be only the theoretical quantity required to react with all of the oxide present, but normally some excess of water is preferred, particularly because some water will be carried away by the effluent chlorinated solvent. Where such water would be undesirable in the process to which the purified effluent is directed, an intermediate drying step of any conventional design may be used to remove it.

In order to obtain substantially complete reaction of the olefin oxide component and retention of the diol product in the resin bed, a contact time of appreciable length is required. It has been found that to provide at least about 95 percent removal of olefin oxide present in a solvent containing a conventional concentration of that stabilizer, the maximum flow rate of solvent through the resin bed should be about five volumes of solvent per volume of bed per hour.

The particular advantage of the present process is that both the olefin oxide and the diol hydrolysis product are removed by the resin bed. A resin of the type defined for this process will retain up to about 5 percent of its weight of diol. The resin bed can be washed free of accumulated diol as necessary by periodic flushing with water. This not only flushes out the retained diol but maintains the resin bed in a desirable wet condition.

EXAMPLES 1-3

A 46 cm length of 1.3 cm diameter Monel pipe was filled with about 50 ml of wet DOWEX 50WX4, H+ form cation exchange resin. Inhibited 1,1,1-trichloroethane containing 315 ppm by weight 1,2-butylene oxide was pumped upward through the vertical resin bed at different rates with the butylene oxide content of the effluent liquid determined at each flow rate by gas chromatographic analysis. The resin bed and the 1,1,1-trichloroethane were both at room temperature.

Table

| Example No. | Flow Rate Bed Vol/Hr | Effluent ppm BO |
| --- | --- | --- |
| 1 | 1.0 | 2.0 |
| 2 | 3.0 | 8.0 |
| 3 | 7.0 | 55.0 |

In each case, the effluent solvent was essentially free of the butanediol hydrolysis product.

By the same procedure as illustrated above, small concentrations of olefin oxides such as propylene oxide, glycidol, epichlorohydrin, cyclohexene oxide, and styrene oxide are effectively removed from 1,1,1-trichloroethane or other chlorinated solvents as previously described.

We claim:

1. A method for removing an olefin oxide of 3-8 carbon atoms from a chlorinated lower aliphatic hydrocarbon containing a small amount of said oxide by contacting the liquid chlorinated hydrocarbon with the hydrogen form of a strong acid cation exchange resin in the presence of water, thereby converting said olefin oxide to the corresponding diol, and washing the resin periodically with water, thereby separating accumulated diol from the resin.

2. The method of claim 1 wherein the chlorinated hydrocarbon is 1,1,1-trichloroethane.

3. The method of claim 2 wherein the olefin oxide is butylene oxide.

4. The process of claim 1 wherein the olefin oxide is propylene oxide, epichlorohydrin, glycidol, butylene oxide, cyclohexene oxide, or styrene oxide.

5. The process of claim 1 wherein the chlorinated hydrocarbon is contacted with the cation exchange resin at a maximum flow rate of about five volumes of chlorinated hydrocarbon per volume of resin per hour.

6. The process of claim 1 wherein the chlorinated hydrocarbon contains about 0.01–5 weight percent of olefin oxide.

* * * * *